United States Patent [19]
Klinkhammer

[11] Patent Number: 5,316,027
[45] Date of Patent: May 31, 1994

[54] STRADDLE TYPE TOOTH BRUSHING DEVICE
[75] Inventor: Ronald W. Klinkhammer, Seattle, Wash.
[73] Assignee: Oral Logic, Inc., Seattle, Wash.
[21] Appl. No.: 924,099
[22] Filed: Aug. 3, 1992

Related U.S. Application Data

[63] Continuation-in-part of Ser. No. 664,487, Mar. 4, 1991, Pat. No. 5,137,039, which is a continuation of Ser. No. 145,771, Jan. 19, 1988, and a continuation-in-part of Ser. No. 499,022, Mar. 26, 1990, Pat. No. 5,171,066.
[51] Int. Cl.⁵ .......................................... A45D 44/18
[52] U.S. Cl. .................................. 132/308; 132/309; 15/167.1; 15/167.2
[58] Field of Search ............... 132/308, 309; 15/220.1, 15/167.1, 167.2, 110, 159 A; 128/62 A, 66

[56] References Cited

U.S. PATENT DOCUMENTS

| | | | |
|---|---|---|---|
| 301,644 | 7/1884 | Thompson | 128/62 A |
| 715,263 | 12/1902 | Haussmann | 128/62 A |
| 864,054 | 8/1907 | Abrams | 15/167.2 |
| 1,389,624 | 6/1920 | Carroll | 15/167.2 |
| 1,599,339 | 9/1926 | Loyd | 15/167.2 |
| 1,668,385 | 5/1928 | Szekely et al. | 15/167.2 |
| 1,709,262 | 4/1929 | Henderhan | 15/167.2 |
| 2,139,245 | 12/1938 | Ogden | 128/62 A |
| 2,196,284 | 4/1940 | Ackerman | 128/62 A |
| 2,317,485 | 4/1943 | Rider | 15/167.1 |
| 2,625,697 | 1/1953 | Cyser | 15/167.1 |
| 2,660,745 | 12/1953 | Yusko | 15/167.1 |
| 2,766,750 | 10/1956 | Darcissac | 128/62 A |
| 2,807,820 | 10/1957 | Dinhofer | 15/167.1 |
| 3,103,027 | 9/1963 | Birch | 15/110 |
| 3,103,679 | 9/1963 | Clemens | 15/167.1 |
| 3,368,553 | 2/1968 | Kirby | 128/62 A |
| 3,398,421 | 8/1968 | Rashbaum | 15/167.2 |
| 3,509,874 | 5/1970 | Stillman | 128/62 A |
| 3,631,869 | 1/1972 | Espinosa | 132/323 |
| 3,640,291 | 2/1972 | Mizuno | 132/309 |
| 3,732,589 | 5/1973 | Burki | 15/167.2 |
| 3,879,139 | 4/1975 | Dahl et al. | 401/135 |
| 3,953,907 | 5/1976 | Froidevaux | 15/167.2 |
| 4,263,691 | 4/1981 | Pakarnseree | 15/167.1 |
| 4,449,266 | 5/1984 | Northemann et al. | 15/167 A |
| 4,486,914 | 12/1984 | Planten et al. | 15/167.2 |
| 4,488,328 | 12/1984 | Hyman | 15/167.1 |
| 4,535,761 | 8/1985 | Rabinowitz | 128/62 A |
| 4,610,045 | 9/1986 | Rauch | 15/167.1 |
| 4,625,357 | 12/1986 | DeMartino | 15/167.1 |
| 4,638,520 | 1/1987 | Eickmann | 15/22.1 |
| 4,654,922 | 4/1987 | Chen | 15/172 |
| 4,691,405 | 9/1987 | Reed | 15/201 |

OTHER PUBLICATIONS

Definition; Illustrated Dictionary of Dentistry pp. 822–823, 1982.

Primary Examiner—Gene Mancene
Assistant Examiner—Frank A. LaViola
Attorney, Agent, or Firm—Christopher Duffy

[57] ABSTRACT

Earlier devices of the genre, had a yoke-like head for brushing the teeth, and a cowling of reentrantly folded flexible material interconnected with the arms of the head so as to straddle the slot between the arms. The midsection at the bight of the cowling had pleats between it and the wings of the cowling, and together they formed an articulated linkage between the wings for preserving the bias on the wings during the tooth brushing operation. In the present device, the arms 12 have only brackets 34 on the terminal end portions thereof, the relatively outboard portions 38 of which elbow out in front of the arms, like cowcatchers, below the terminal ends 20 of the arms. The portions 38 in turn have mitt-like brushes 50 thereon comprised of fields of spaced individual bristle of 0.010 inch in diameter or greater at the bases 64 thereof, collectively firm but individually spaced apart from one another at heights and densities enabling them to laterally deflect within the fields, and made of a thermoplastic resin material which is 47 or less in durometer on the Shore D Scale, so as to be ultra soft to the gums of the teeth. Now, with brackets so equipped, the arms 12 can forcibly pinch the portions 38 of the brackets together to the extent that the brushes 50 maintain a firm but comfortable grip on a row of teeth 3 at the level of the gingival sulcus 51 thereof, notwithstanding the absence of the linkage. Moreover, the arms and brackets can be pivoted crosswise the length of the row, to be oscillated through a pitman arm-like motion more in parallel to the gaps between pairs of teeth.

20 Claims, 3 Drawing Sheets

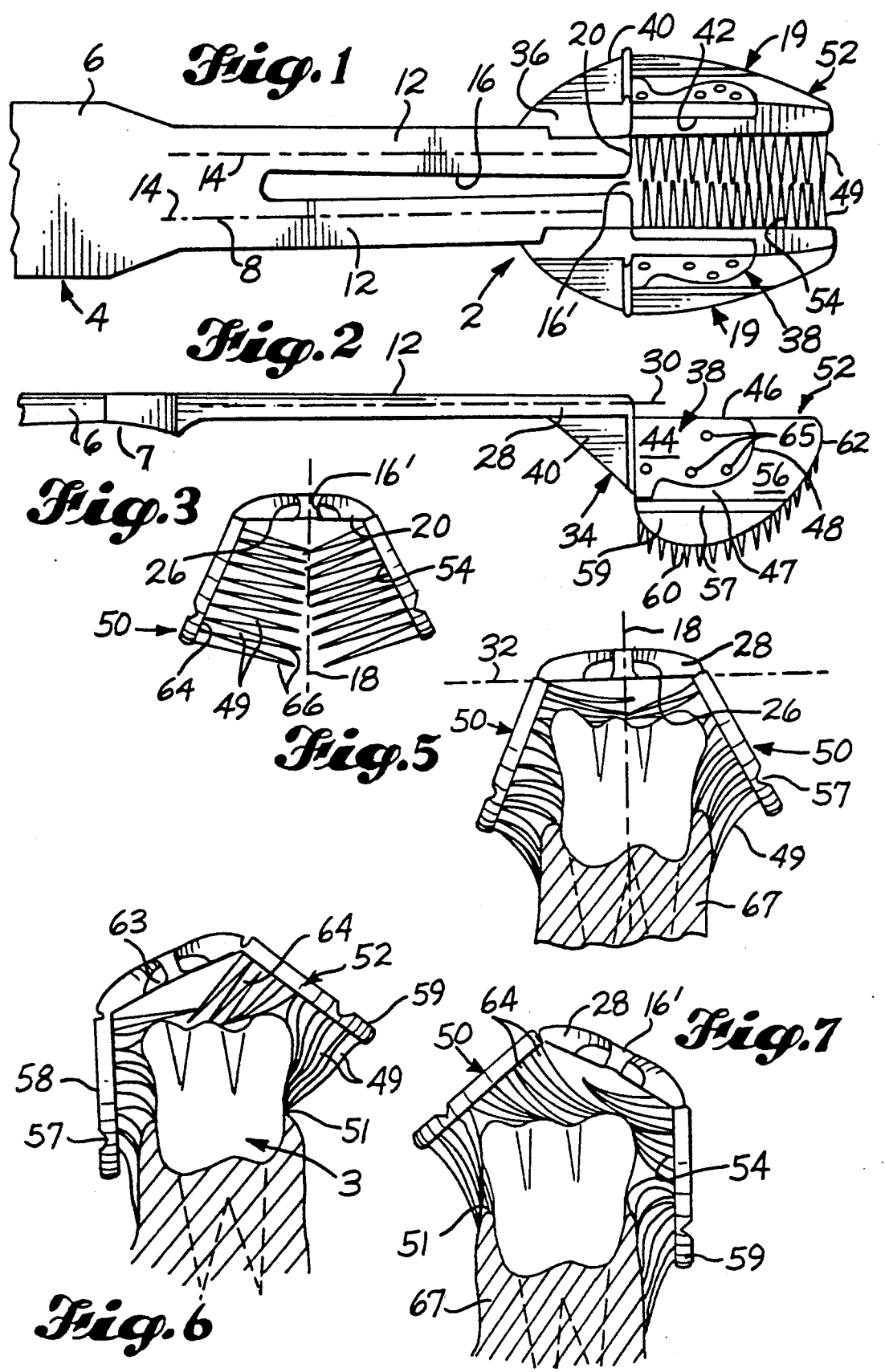

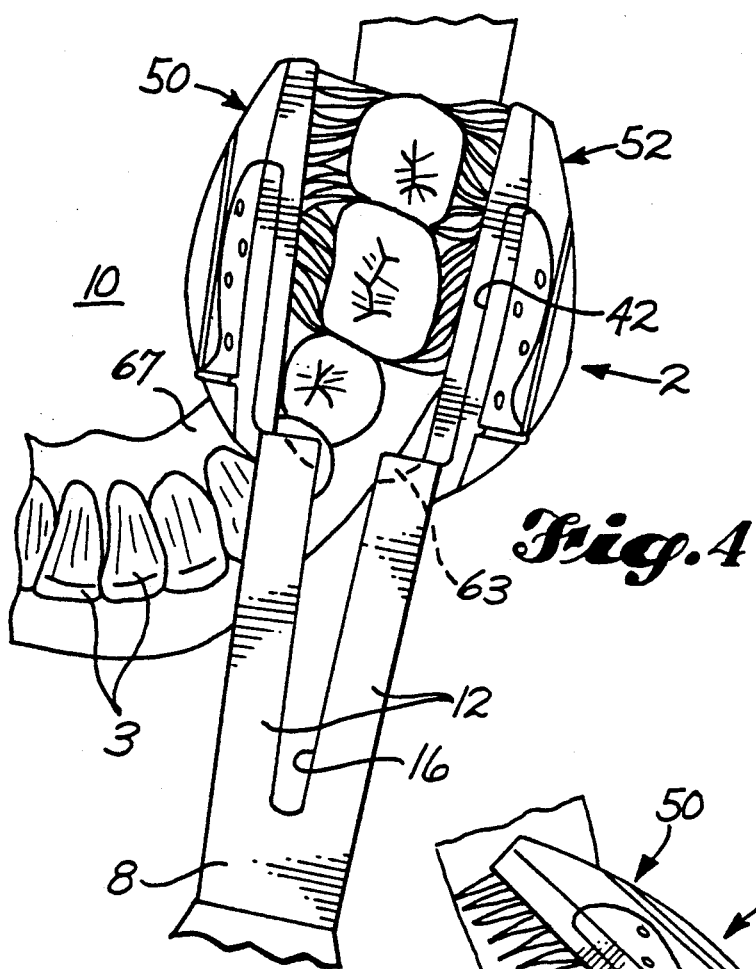
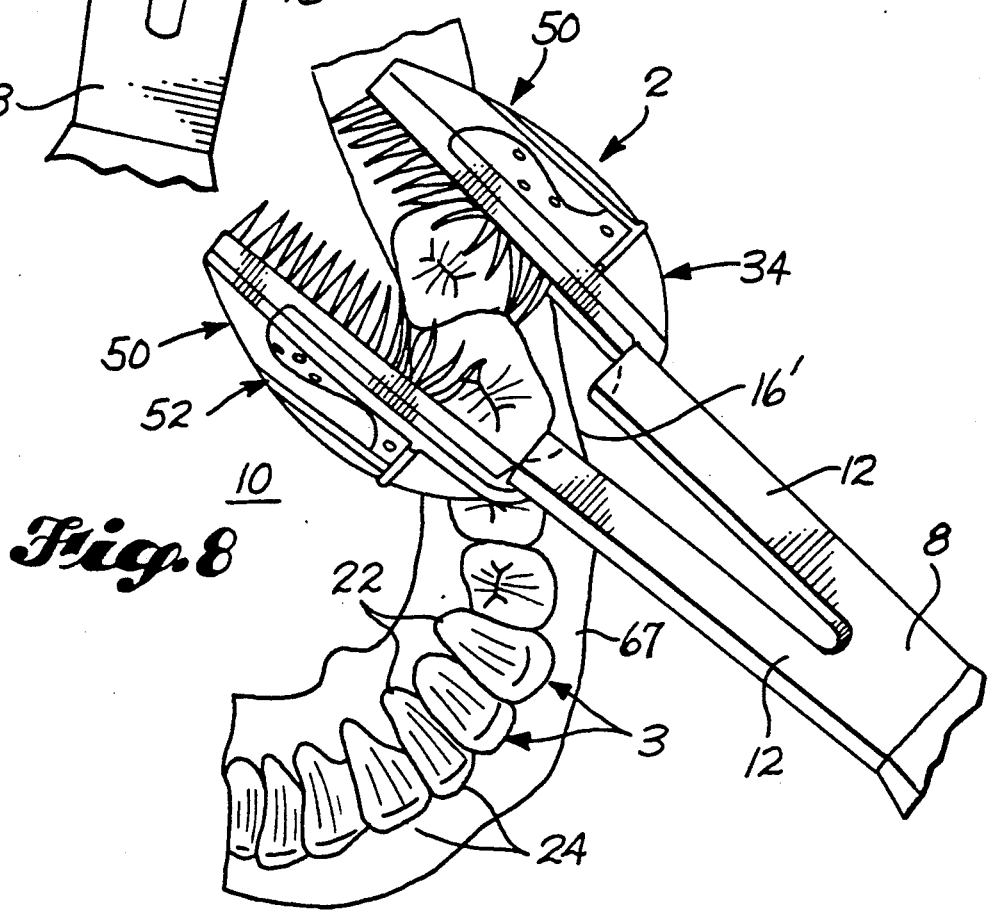

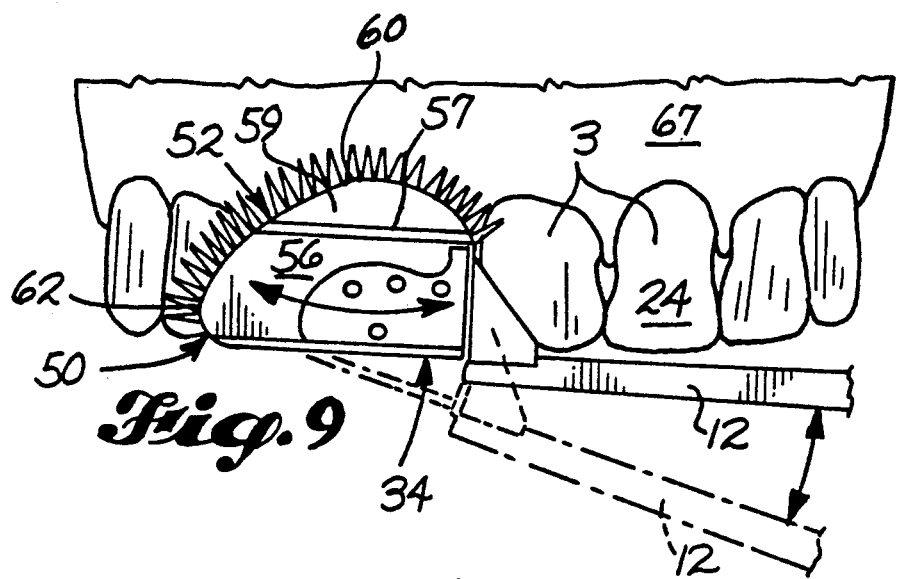
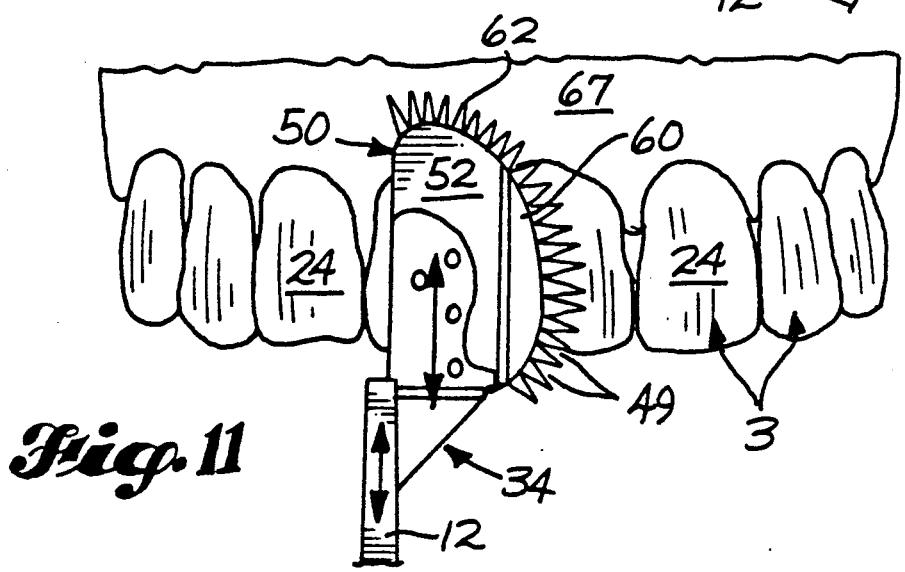
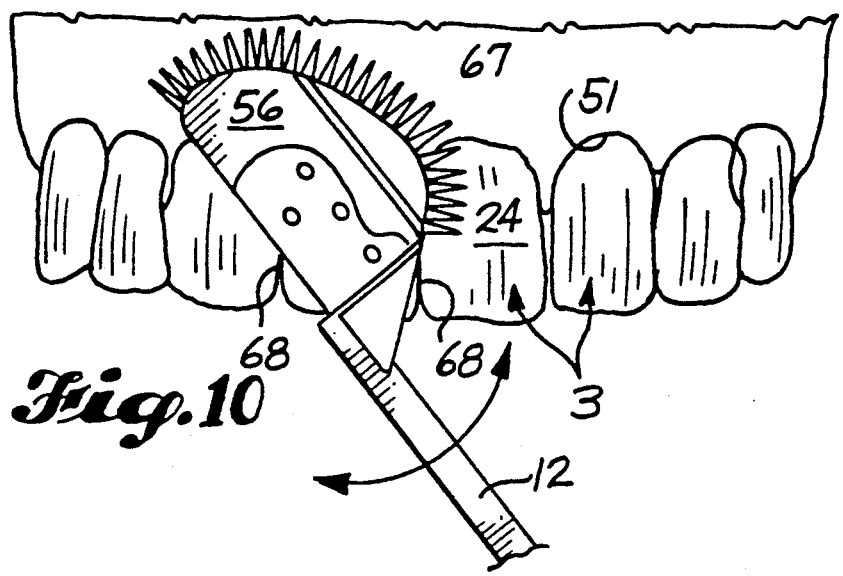

STRADDLE TYPE TOOTH BRUSHING DEVICE

DESCRIPTION

1. Related Applications

The present invention is a continuation-in-part of my application Ser. No. 664,487, now U.S. Pat. No. 5,137,039 filed on Mar. 4, 1991 and having the title TOOTH CLEANING DEVICE AND METHOD. Application Ser. No. 664,487 is in turn a continuation of my application Ser. No. 145,771 now abandoned filed on Jan. 19, 1988 and having the same title. The present Application is also a continuation-in-part of my application Ser. No. 499,022 now U.S. Pat. No. 5,171,066 filed on Mar. 26, 1990 and having the title TOOTH CLEANING DEVICE AND METHOD FOR MAKING THE SAME.

2. Technical Field

This invention relates to a straddle-type tooth brushing device, and in particular, to a tooth brushing device of this type wherein there are means including a pair of elongated arms having brushes on the distal end portions thereof forming a head for straddling about a row of teeth to be cleaned, elongated support means including a handle, for supporting the head adjacent the row of teeth, and biasing means acting on the distal end portions of the arms from within the head to yieldably bias the brushes into engagement with the relatively inside and outside faces of the teeth when the head is straddled about the row thereof. The arms have longitudinal axes and are rigidly interconnected with the support means so as to form relatively rigid longitudinal extensions thereof, which project from the distal end of the support means in generally spaced parallel relationship to one another, and have an elongated slot in the space therebetween which opens to the outside of the device at the distal end portions of the arms, and has a central plane therein which extends between the longitudinal axes of the arms generally parallel thereto. The distal end portions of the arms have relatively laterally inwardly directed surfaces thereon which are relatively opposed to one another across the central plane of the slot and extend in planes generally parallel to the longitudinal axes of the arms, with relatively upper, lower and forward edges thereabout at the peripheries thereof, which are disposed relatively remote from, and adjacent to, the gum lines of the respective row of teeth being brushed, and forwardly of the surface, respectively, when the head is straddled about the row of teeth so that the central plane of the slot is aligned with the row of teeth. The brushes comprise discrete strands of thermoplastic resin material which are relatively upstanding on the relatively laterally inwardly directed surfaces of the distal end portions of the arms at individually spaced apart locations on the surfaces so as to be individually laterally deflectable in relation to one another, yet collectively operable on the respective surfaces to form mutually opposing fields of bristle for tooth brushing purposes when the head is straddled about a row of teeth and the brushes are engaged with the faces of the teeth. The arms are constructed of a stiff but resiliently flexible material, and the distal end portions of the arms are yieldably biased relatively toward one another by the biasing means, transverse the central plane of the slot in the relaxed state of the arms, to the extent that the user must forcibly wedge the teeth between the fields of bristle when inserting the teeth between the brushes to straddle the head about the row of teeth. As a consequence, the distal end portions of the arms take a pincers-like grip on the teeth transverse the row thereof, when the head is straddled about the row of teeth, and the user need not use his thumb and forefinger, nor any other part of his hand, to assert a grip on the teeth. Instead, his hand may remain on the handle of the device throughout the tooth brushing operation, and this facilitates manipulating the device since his hand need not be advanced forwardly onto the arms for purposes of asserting a grip, as was necessary in the prior art.

3. Background Art

Commercial versions of the device were placed on sale in October 1990, and have received widespread acceptance in the marketplace since then.

DISCLOSURE OF THE INVENTION

I have since found that the articulated linkage in the earlier devices, can be dispensed with, and the arms terminated at the upper, lower and forward peripheral edges of the relatively laterally inwardly directed surfaces of the distal end portions of the arms, so that the respective arms are independent of one another transverse the central plane of the slot, to enable the device to undergo certain additional dynamics in the tooth brushing operation, if (1) the brushes on the surfaces comprise discrete strands of thermoplastic resin material which are 47 or less in durometer on the Shore D Scale, 0.010 inch in diameter or greater at the bases thereof, and relatively upstand on the surfaces at individually spaced apart locations on the surfaces so as to be individually laterally deflectable in relation to one another, yet collectively operable on the respective surfaces to form mutually opposing fields of bristle that are firm enough for tooth brushing purposes but ultrasoft to the gingival sulcus at the gum lines of the teeth when the head is straddled about a row of teeth and the brushes are engaged with the faces of the teeth, and (2) the distal end portions of the arms are so closely spaced apart from one another at the surfaces, and so yieldably biased relatively toward one another by the biasing means, transverse the central plane of the slot in the relaxed state of the arms, that the user must forcibly wedge the teeth between the fields of bristle when inserting the teeth between the brushes to straddle the head about the row of teeth.

One way to provide the bias is to use a head wherein (1) the arms have main portions which cantilever from the distal end of the support means and terminate independently of one another at points relatively remote from the distal end of the support means where the slot has less than a tooth in width transverse the central plane of the slot, and (2) the main portions of the arms have extensions thereon which cantilever relatively laterally outwardly from the terminal end portions of the main portions to greater than a tooth in width on the opposing sides of the central plane of the slot, and have relatively outboard portions thereof which project relatively outwardly beyond the terminal ends of the main portions in directions relatively away from the distal end of the support means longitudinally thereof, to form distal end portions of the arms which are spaced apart from one another at the relatively laterally inwardly directed surfaces thereof and yieldably biased toward one another at said surfaces by the main portions, transverse the central plane of the slot in the relaxed state of the arms, to the extent that the user must forcibly wedge the teeth between the fields of bristle to straddle the row of teeth.

For optimal firmness, the strands of bristle preferably upstand on substrates of the same resin material which cover the relatively laterally inwardly directed surfaces of the distal end portions of the arms in their entireties. In fact, in certain of the presently preferred embodiments of the invention, the brushes comprise monoliths of the thermoplastic resin material, which substantially encircle the distal end portions of the arms at the relatively laterally inwardly and outwardly directed surfaces thereof, and the relatively upper and lower peripheral edges thereof, and have the strands of bristle relatively monolithically upstanding on the relatively opposing inside surfaces of the monoliths, for engagement with the faces of the teeth. Also, in many of these embodiments, the monoliths have portions thereof which project relatively outwardly beyond and below the relatively forward and lower peripheral edges of the distal end portions of the arms, and form relatively depending lobes thereon consisting of the resin material alone, for engaging the sulcus and the gingiva of the teeth. In some embodiments, moreover, the relatively remote outside surfaces of the monoliths have grooves thereacross which subdivide the lobes into main body portions, and bottom portions therebelow which are hinged to the main body portions of the lobes for deflection by the gums in the tooth brushing operation.

Preferably, the relatively bottom and leading edges of the lobes, relative to the gum lines of the teeth, are arcuately rounded; and preferably, the longitudinal axes of the arms are substantially coplanar with one another in a first cross sectional plane of the arms extending substantially normal to the central plane of the slot, and the terminal ends of the main portions of the arms are angled to the first cross sectional planes of the arms at the relatively inner peripheral edges thereof on the slot.

In most of the presently preferred embodiments of the invention, the relatively laterally inwardly directed surfaces of the distal end portions of the arms are disposed at acute angles to the central plane of the slot in the direction relatively upwardly of the plane, and the strands of bristle are angled to the central plane of the slot in the opposite direction so that the fields of bristle incline apically to the gingival sulcus of the teeth, at approximately 45 degrees when the head is straddled about a row of teeth. In the relaxed state of the arms, however, the strands of bristle approach the central plane of the slot at greater than 45 degrees, and may even interdigitate with one another at the tops of the fields.

Preferably, the resin material has a hardness of about 24–27 on the Shore D Scale, depending on the diameter of the strands of at the bases thereof. Preferably too, the resin material has a Vicat softening temperature of 140 degrees F or greater.

In many of the presently preferred embodiments of the invention, the thermoplastic resin material is a polyolefin; and in certain of them, the material is a copolymer of ethylene and vinyl acetate, and the amount of vinyl acetate monomer in the copolymer is adjusted to constitute about 9–28% by weight of the total gross amount of the copolymer, depending on the diameter of the strands at the bases thereof. In one group of embodiments, for example, the strands have a diameter of 0.040 inch at the bases thereof, and the vinyl acetate monomer constitutes about 18–25% by weight of the total gross amount of the copolymer.

Preferably, the strands of are tapered from the bases thereof to a lesser diameter at the tips thereof. In certain of the presently preferred embodiments of the invention, they are conical and tapered to a point along the length thereof intermediate the bases and the tips thereof, and then tapered at an increased draft from the intermediate points thereof to the tips thereof.

For the best combination, the longitudinal axes of the arms are substantially coplanar with one another in a first cross sectional plane of the arms extending substantially normal to the central plane of the slot at the terminal end portions of the main portions of the arms, those sides of the terminal end portions of the main portions of the arms which are disposed relatively adjacent to the gum lines of the row of teeth being brushed, are substantially coplanar with one another in a second cross sectional plane of the arms extending substantially normal to the central plane of the slot, and the extensions of the main portions of the arms take the form of brackets which have successively interconnected inboard and outboard portions, the relatively inboard portions of which project relatively laterally outwardly from the terminal end portions of the main portions of the arms, and the relatively outboard portions of which relatively depend from the relatively inboard portions of the brackets, and cantilever relatively outwardly beyond the terminal ends of the main portions of the arms in directions relatively away from the distal end of the support means longitudinally thereof, on the opposite side of the second cross sectional plane of the arms from the first cross sectional plane thereof. This has the effect of dog-legging the relatively outboard portions of the brackets in front of the terminal end portions of the main portions of the arms at a level relatively below the lower sides thereof, so that the relatively outboard portions of the brackets can be translated like cowcatchers along the length of a row of teeth, in juxtaposition with the relatively inside and outside faces thereof, and then when desired, pivoted into positions more parallel to the gaps between pairs of teeth, so that they then can be put through a pitman arm-like motion, crosswise the length of the row of teeth, to add a vertical component to their action.

In some of the presently preferred embodiments of the invention, the arms are also fabricated from plastic resin material. Furthermore, in many of these embodiments, the support means and the arms are fabricated as a monolithic frame having the brushes molded therearound on the distal end portions of the arms.

BRIEF DESCRIPTION OF THE DRAWINGS

These features will be better understood by reference to the accompanying drawings wherein I have illustrated one of the presently preferred embodiments of the invention, as well as certain of the dynamics through which it can be put in a tooth brushing operation.

In the drawings:

FIG. 1 is a top plan view of the device, but with a portion of the handle omitted so that the head of the device can be more greatly enlarged in the drawing;

FIG. 2 is a side elevational view of the device, but again, with a portion of the handle omitted;

FIG. 3 is a front elevational view of the head of the device in the relaxed state of the same;

FIG. 4 is a top plan view of the head of the device when the head has been straddled about a lower row of teeth in a tooth brushing operation;

FIG. 5 is a cross sectional view of the lower row of teeth, when the head of the device is straddled upright to the teeth;

FIG. 6 is a similar cross sectional view of the lower row of teeth, when the head has been rotated to one side of the row to apply the bristle of the head more directly to the gum line on that side;

FIG. 7 is similar to FIG. 6 but with the head of the device rotated to the opposite side to apply the bristle more directly to that side;

FIG. 8 is similar to FIG. 4, but shows the application of the head of the device to the endmost tooth of the row;

FIG. 9 is a front elevational view of the upper row of teeth when the head of the device has been straddled about the row in parallel to the length thereof, but also illustrating in phantom the capability of the head to be angled to the length of the row;

FIG. 10 is a similar view of the upper row of teeth when the head of the device has been rotated more fully from the phantom view of it in FIG. 9, and is undergoing the pitman arm-like motion of which it is capable, and FIG. 11 is a third front elevational view of the upper row of teeth when the head of the device has been rotated to coincide with a perpendicular to the row, such as for brushing the frontmost teeth of the row, on parallels to the gaps between pairs of teeth.

BEST MODE FOR CARRYING OUT THE INVENTION

Referring to the drawings, it will be seen that in general the device comprises a yoke-like head 2 for brushing the teeth 3, and elongated support means 4, such as a handle 6 having a "thumbprint" 7 and a shank 8 on the distal end thereof, for supporting and manipulating the head 2 in the mouth 10 of the person whose teeth 3 are to be cleaned in a tooth brushing operation. The head 2 comprises a pair of elongated arms 12 which have longitudinal axes 14, and are rigidly interconnected with the shank 8 so as to form relatively rigid longitudinal extensions thereof, which project from the distal end of the shank in generally spaced parallel relationship to one another so as to be insertable in the person's mouth, side by side of one another, when the device is put to use in a tooth brushing operation. The space between the arms forms an elongated slot 16 which opens to the outside of the device at the end 16' thereof that is relatively remote from the distal end of the shank, and the slot has a central plane 18 which extends longitudinally thereof between the terminal ends 20 of the arms. Outriggered on the ends 20, and mutually opposed to one another across the plane 18 of the slot, is a pair of tooth brushing members 19 which are adapted to be straddled about a row of teeth 3 in the person's mouth, and translated along the length of the row in juxtaposition to the relatively inside and outside faces 22 and 24 of the teeth, respectively, when the arms are manipulated in the tooth brushing operation so that the plane 18 is generally aligned with the row of teeth, as in FIGS. 4-7 and 9-11.

The terms "upper" and "lower" will be used hereafter to refer to certain features of the head 2 which when the device is put to use, are disposed relatively remote from, and adjacent to, the gum lines of the respective row of teeth being brushed, respectively. The term "forward" refers to those features of the head which are relatively remote from the distal end of the shank in use.

Referring now to FIGS. 1-7 in particular, it will be seen that the arms 12 of the head 2 terminate independently of one another at the ends 20 thereof relatively remote from the shank 8 of the handle 6, and both the longitudinal axes 14 of the respective arms, and the lower sides 26 of the terminal end portions 28 of the main portion of the respective arms, are substantially coplanar with one another in first and second cross sectional planes 30 and 32 of the arms, respectively, which extend substantially normal to the central plane 18 of the slot at the terminal end portions 28 of the arms. The end opening 16' of the slot 16, meanwhile, is less than a tooth in width transverse the central plane 18 of the slot, but in lieu of greater width, the terminal end portions 28 of the arms have brackets 34 thereon which cantilever relatively outwardly from the arms on the opposing sides of the central plane 18 of the slot, to form wing-like extensions of the arms which can be straddled about a row of teeth, transverse the length thereof, and translated along the length of the row for the tooth brushing operation, as shall be explained. The brackets 34 have successively interconnected relatively inboard and outboard portions 36 and 38, respectively, as well as relatively intermediate portions 40 therebetween. The relatively inboard portions 36 project relatively laterally outwardly from the terminal end portions 28 of the arms, and the relatively intermediate portions 40 of the brackets are outriggered like gusset plates on them. The relatively intermediate portions 40 are also reentrantly folded about the axes 14 of the arms, so as to relatively depend from the relatively inboard portions 36 at acute angles to the central plane 18 of the slot, and for the most part on the opposite side of the second cross sectional plane 32 of the arms from the first cross sectional plane 30 thereof. The relatively outboard portions 38 of the brackets are in turn cantilevered relatively rigidly outwardly from the forward edges of the intermediate portions, and relatively rigidly outwardly beyond the terminal ends 20 of the arms, in directions relatively away from the distal end of the shank 8 of the handle, longitudinally thereof. They also project at the same angles that the intermediate portions 40 have to the plane 18, and at locations on the opposite side of the second cross sectional plane 32 of the arms from the aforesaid first cross sectional plane 30 thereof. In this disposition, the relatively outboard portions 38 of the brackets have pairs of relatively laterally inwardly and outwardly directed surfaces 42 and 44 thereon, respectively, which in turn have upper, lower and forward edges 46, 47 and 48 thereabout, at the peripheries thereof. Moreover, the relatively laterally inwardly directed surfaces 42 of the portions 38 are relatively opposed to one another, across the central plane 18 of the slot, and extend in planes generally parallel to the longitudinal axes 14 of the arms. The tooth brushing members 19 are mounted in turn on the portions 38 so that the portions present fields of bristle 49 to one another at the surfaces 42 thereof, for engagement with the faces 22, 24 of the teeth in the tooth brushing operation.

In the device disclosed in the earlier Applications, the relatively outboard portions 38 of the brackets were part of the cowling, and thus were interconnected with one another at the relatively upper peripheral edges 46 of their relatively opposing inside surfaces 42. Contrary to the invention disclosed in those Applications, however, the relatively outboard portions 38 of the brackets in the present device are terminated at both the relatively upper and lower peripheral edges 46, 47 of the relatively opposing inside surfaces 42 thereof, as well as at the forward edges 48 thereof, so as to increase the range of dynamics through which the device can be put in the tooth brushing operation. This is possible because the strands of bristle 49 on the brackets have an unusually low durometer hardness, yet firmness as well, which makes it possible to pinch the brackets together to the extent that they no longer need the articulated linkage of the cowling to retain a firm but comfortable grip on the teeth in the tooth brushing operation. If necessary or desired, moreover, the user can adjust the hardness of the bristle at the time of use, to render them more suitable to his level of comfort, as shall be explained.

More specifically, the relatively outboard portions 38 of the brackets are now equipped with firm but ultra soft brushes 50 of thermoplastic resin material on the relatively opposing inside surfaces 42 thereof; and to take advantage of the ultra soft but firm body characteristics of the bristle 49 in the brushes, the arms 12 which operate to pinch the brushes together are constructed of a stiff but resiliently flexible material, which is of such lengths inward along the slot 16 from the end opening 16, thereof and relative to the widths of the arms transverse the central plane 18 of the slot, that when the brushes are spaced apart from one another transverse the plane 18 of the slot to the extent that the portions 38 of the brackets must once again be straddled about a row of teeth for the tooth brushing operation by relatively wedgibly inserting the teeth between the brushes until the fields of bristle engage the faces of the teeth at the gingival sulcus 51 thereof, the arms 12 and brackets 34 respond, after yielding to the wedgible insertion of the teeth between the brushes, by so forcibly pinching the relatively outboard portions 38 of the brackets relatively toward one another transverse the central plane 18 of the slot, that notwithstanding the absence of the linkage, the brushes 50 maintain a firm but comfortable grip on the teeth at the level of the gingival sulcus when the relatively outboard portions 38 of the brackets are translated along the length of a row of teeth in the tooth brushing operation. Note FIGS. 4–7 and 9–11 in this connection. And in FIG. 1, note also the slight pinch to the slot, in the direction of the end opening 16' thereof. The brushes 50 are in fact glove-like monoliths 52 of thermoplastic resin material, which substantially encircle the relatively outboard portions 38 of the brackets at the surfaces 42, 44 and the edges 46, 47 and 48 thereof, and have fields of spaced individual strands of bristle 49 relatively monolithically upstanding on the relatively opposing inside surfaces 54 thereof, much like the wings of the cowling which was formed on the device of application Ser. No. 499,022. There are also portions of the monoliths which project well outwardly beyond and below the relatively forward and lower peripheral edges 46 and 47 of the portions 38 of the brackets, so as to form lobes 56 thereon consisting of the resin alone, which relatively depend from the bottom edges 46 of the portions 38, and project relatively forwardly from the forward edges 48 thereof. The lobes are also equipped with bristle, but are relatively "spineless" since the harder portions 38 of the brackets are disposed well above and behind them. This "spinelessness" leaves the lobes relatively limp and flaccid, and more easily deflectable crosswise the plane 18 of the slot, when the device is put to use. The lobes 56 may also have grooves 57 extending thereacross, at the relatively remote outside surfaces 58 thereof, which if deepened enough, will allow the relatively bottom portions 59 of the lobes to flap with respect to the main bodies of the monoliths, for reasons which will be explained.

The relatively bottom and relatively leading edges 60, 62 of the lobes 56 are also arcuately rounded about points disposed somewhat ahead of the terminal ends 20 of the arms, so that even the outline of the monoliths lends itself to the new dynamics of the device, as shall be explained. And for related reasons, the terminal ends 20 of the arms are mitered or chamfered to the planes 30 and 32 of the arms, at the relatively inner peripheral edges 63 thereof on the slot 16.

Preferably, the relatively opposing inside surfaces 54 of the brushes are disposed at acute angles to the central plane 18 of the slot 16, in the direction relatively upwardly thereof, and the fields of bristle 49 are angled to the plane of the slot in the opposite direction, so that they will incline apically to the gingival sulcus 51 of the teeth, at approximately 45 degrees, when the brackets 34 of the device are straddled about a row of teeth in the manner of FIGS. 4 and 5. In the relaxed state of the device, however, the fields of bristle more closely approach the plane 18 of the slot, and may even interdigitate with one another at the tops thereof, as seen in FIG. 3.

Unlike conventional extruded and tufted bristle of Nylon or the like, the strands of bristle 49 in my brush have a far greater diameter of at least 0.010 inch at the bases 64 thereof; and when collected in fields for firmness, but individually spaced apart from one another at heights and densities enabling them to laterally deflect within the fields, this diameter enables the resin in the brushes to have a hardness or durometer of only about 24–47 on the Shore D Scale, depending on the actual diameter of the bristle at the bases thereof. This hardness is so low, of course, that the actual choice must be tempered by the practical considerations of marketing and point of use, lest the highly temperature sensitive resin soften to the point of distortion, for example, in the transport of the device to the marketplace. Therefore, the choice is commonly one in which the resin also has a Vicat softening temperature that is adapted to be form-sustaining for the marketing and point of use of the device, such as, for example, one of 140 degrees F. or greater for the United States.

At the point of use however, the temperature sensitivity of the bristle actually has a positive side, in that the bristle may be briefly subjected to heat—or cold—such as under hot or cold tap water for a few seconds, by way of softening—or hardening—the bristle even more for the tooth brushing operation.

The handle 6, sheath 8, arms 12 and brackets 34 of the device are commonly also fabricated from plastic resin material, but one which, of course, has the differing properties needed for them. Commonly, the handle, shank, arms, and brackets are fabricated as a monolithic frame, and then mitt-like brushes such as those seen at 50 in the drawings are molded around the relatively outboard portions 38 of the frame, using the process disclosed in application Ser. No. 499,922. Note the spacer studs 65 incorporated into the brushes from that process.

Polyolefins are one choice of thermoplastic resin for the brushes 50 when this process is used. In the process of application Ser. No. 499,922, for example, I have used certain copolymers of ethylene and vinyl acetate, and to get the desired hardness, have adjusted the amount of vinyl acetate monomer to constitute about 9-28% by weight of the total gross amount, depending on the diameter of the bristle at the bases thereof. I have taken care, however, that the resin also has a sufficiently high Vicat softening temperature to sustain its form in the marketing and use of the device. The Industrial Polymers Division of the DuPont Company of Wilmington, Del., 19898, provides a wide range of such copolymers under the trademark ELVAX, and I have used either selected semi-transparent or clear resins from among the group, or blends thereof, and I have found that both are highly suitable for my purposes. For example, when the strand of bristle in the fields of the same have a 0.040 inch diameter at the bases thereof, and are distributed at 0.010-0.025 inch spacings in the field, an ELVAX resin having an 18-25% vinyl acetate content by weight to the gross amount of the copolymer, will provide a suitable combination of softness and firmness to the bristle. I have also blended 30% of UE 634 from Quantum Chemical Corporation's USI Division at Rolling Meadows, Ill., 60008, with 70% of UE 652 from Quantum, and I have achieved fully satisfactory results from the blend. The U 652 has an 19% vinyl acetate content by weight, and the UE 634 a 28% vinyl acetate content by weight. Generally, as the diameter of the strands of bristle is decreased at the bases thereof, the vinyl acetate content is correspondingly decreased to get a satisfactory softness, but collective firmness in the fields of bristle. When the bristle diameter drops to as low as 0.010 inch, then DuPont's ELVAX 770 with a vinyl acetate content of 9.5% by weight can be employed in making up the resin material; and when the diameter rises to as much as, for example, 0.060 inch at the bases of the strands of bristle, DuPont's ELVAX 150 having a vinyl acetate content of 33% by weight, can be employed, but only when blended with some other lower content ELVAX resin which will raise the Vicat softening temperature to one which is acceptable for the marketing and use to be made of the device. ELVAX 150 has a Vicat softening temperature as low as 97% F., and in practice, a device with brushes of such a resin material thereon would be extremely difficult to market, so much as use, inasmuch as the brushes might very well melt when standing in the open sun in a shipping container, or on a truck, or when shipped to a country such as Mexico. Therefore, the selection of the resin material must always be a function of the marketing and use to be made of the device, including the location where it is to be put to use.

To a far lesser extent, the choice of resin material is also a function of the height of the bristle. Conventional extruded Nylon tufted bristle are commonly 0.40 inch high. To be effective, bristle require at least 0.25 inch in height. I have employed bristle in the range 0.25-0.35 inch for an adult device and 0.22-0.32 inch for a children's device. In the range 0.22-0.40 inch, the foregoing resin selection is fully operable, but I prefer a bristle length of 0.35 inch for adults and 0.32 inch for children. I also prefer a resin providing a Vicat softening temperature of about 140 degrees F., and in accordance with that, one having a hardness of about 28-38 on the Shore D Scale.

When using the process of application Ser. No. 499,922, the brushes 50 are molded around the relatively outboard portions 38 of the brackets by the injection molding process described therein; and in accordance with that process, the bristle are tapered from the bases thereof to a lesser diameter at the tips 66 thereof. In fact, I have found that they commonly need at least 2% of draft to be parted from the injection mold; and in order to transfer the load at the tip of each bristle to a point part way up the length of the same, for stability, I commonly provide a conical bristle which is 0.040 inch in diameter at the base and 0.350 inch high, and which has about 1% of taper per side for ⅝ the length of the bristle from the bases thereof, and then about 1.5% of taper per side from that point upward to the tips of the bristle. At the ⅝ point, therefore, the bristle approximate 0.036 inch in diameter, and at the tips thereof, 0.010 inch in diameter.

For comparison, even the scrub brushes used in toilets are commonly extruded from Nylon at far less than 0.010 inch throughout their lengths. My bristle are considerably wider than these, therefore, and are even wider at their tips. But given the material of which they are made, and their monolithic character with their substrates 52, the bristle provide the collectively firm but ultra soft body characteristics needed for their tooth brushing function when the arms 12 of the device are constructed and sized as indicated to forcibly pinch the relatively outboard portions 38 of the brackets together to the extent that the brushes 50 maintain a firm but comfortable grip on the teeth when the brackets are translated along the length of a row in a tooth brushing operation.

The bristle 49 also provide a better support for toothpaste and powder, than do thin tufted bristle, because of the greater diameter in their bases and the firmness they provide when collected together in fields.

At present I employ certain amorphous polyesters or polypropylene as the resin material for the frame, i.e., the handle, shank, arms, and brackets of the device. One such polyester is the EKTAR DN003 copolyester provided by the Eastman Chemical Division of Eastman Kodak Company at Kingsport, Tenn. An example of a polypropylene is the Tenite polypropylene P404K-038 provided by Eastman Kodak Company. Frames with slots 13/8 inches long and 0.050 inch wide at their end openings 16', and arms 3/16 inch wide, and made of such materials, are presently used for the device.

The Bass technique of tooth brushing has always been a highly recommended, if not preferable, method of brushing one's teeth. Using it, the brush, conventional or otherwise, is translated along each gum line of each row of teeth, at roughly 45 degrees to the elevation of the teeth, so as to "rake" the sulcus 51 of the teeth like a plowshare without damaging the more tender gingival tissue of the gums. Ideally, however, the motion is not simply a continuous one in the lengthwise direction of the row of teeth, but is an oscillatory or back and forth motion in which short strokes are used to collectively advance the brush lengthwise of the row until the last tooth is reached. The object is to generate a "flicking" motion at the tips of the bristle, to dislodge any debris collected at the sulcus, as well as to scrub the faces of the teeth and massage the more tender gingiva. When using the device disclosed in the earlier Applications, an oscillatory motion could be generated lengthwise of each row of teeth, but because of the articulated linkage arched across the tops of the teeth, the device was limited in its ability to generate any vertical component to the "flicking" action of the tips of the bristle. Also, in the case of the teeth of more elderly persons, whose gums had receded over the years, the cowling could not reach the sulcus with the full effect intended for the device; and if the frontmost teeth of a row, at the bight thereof, were closely crowded so as to make for "corners" at the transition between the frontmost and rearmost teeth of the row, the device was rendered largely inoperative for the frontmost teeth because of the difficulty in turning the corners and maintaining contact with the sulcus as each turn was made.

Most of these shortcomings were attributable to the fact that the articulated linkage of the cowling of the device in the earlier Applications, also functioned as a means for determining the "drop" of the wings of the cowling down the faces 22, 24 of each tooth as the device translated thereacross. Referring now to FIGS. 4–11 herein, it will be seen that the terminal ends 20 of the arms 12 now provide the only limit on the depth to which the brushes 50 can reach in gripping the teeth of a row in a tooth brushing operation, and they, the arms, can be pivoted to any angle desired, relative to the length of the row, to adjust the "drop" of the brushes. This is to say, the brushes now resemble cowcatchers that are underslung in front of the ends 20, below the second cross sectional plane 32 of the arms, and the device can not only be driven along the length of each row, as in the past, and quickly but progressively stopped, advanced and stopped again with an oscillatory motion, while the terminal end portions 28 of the arms "ride above" the tops of the teeth; but in addition, when desired, the arms can be relatively lifted and canted or angled to the row, crosswise the length thereof, so as to introduce a shoveling or scooping motion to the oscillatory movement of the brushes, much like that of a pitman arm. This compound movement will arcuately "flick" the tips of the bristle back and forth in the sulcus, with a vertical component, so as to more effectively sweep the debris from the same in the manner illustrated as best possible in FIG. 10. In addition, and at the same time, if desired, the user may also rotate the head of the device to one side or the other of the row of teeth, as in FIGS. 6 and 7, to adjust the "drop" of the corresponding brush down the face of the teeth on that side, and to lightly massage the gums 67 of the teeth while sweeping the sulcus on that side as shown. Significantly, throughout the entire panoply of motion, it is the bristle on the relatively limp, flaccid lobes 56 of the brushes which sweep arcuately up and down, as well as back and forth, along the sulcus and over the tender gingiva of the gums, and do all of the "brushing" in these delicate areas; and of course, this is desirable because the lobes have the least "spine" of all of the components of the head, so as to cause the least irritation to these tender areas. Given grooves 57 of sufficient depth, moreover, the bottom portions 59 of the lobes will be hinged somewhat to the main bodies of the monoliths, so as to be deflected by the gums when they are pressed against them. But to simplify the drawings, this feature is not illustrated per se.

Ultimately, when the user reaches the endmost tooth at each end of each row, he may sharply angle the head of the device to the tooth, horizontally, to scrub the backsides of the tooth, and this is illustrated in exaggerated manner in FIG. 8.

Given his ability to angle the device to the length of each row, and given the offset between the arms and the brushes, the user may also use the device in the manner of FIG. 11 to brush between pairs of teeth on parallels to the gaps 68 therebetween. This is particularly so in the case of the frontmost teeth of a row, and in fact is particularly advantageous in the case of these teeth if they sharply "corner" with respect to the rearmost teeth in the row. Also, the device may be oriented toward one side of the mouth initially, to angle the bristle into the gaps 68 in one direction, and then reversed to angle the bristle in the opposite direction, perhaps exchanging hands for this purpose, if need be. Angled in this way, the device can be worked up and down along the length of a row, to effectively brush the gaps between pairs of teeth, while limited in its "drop" onto the gums of the teeth by the terminal ends 20 of the arms, which serve as a limit stop for the oscillatory motion of the device, as seen in FIG. 11. Of course, the terminal ends 20 of the arms also serve as a limit stop for the scooping action of the brushes when the device is employed in the manner of FIGS. 9 and 10 and rotated as described, but this action commonly has an insufficient vertical component to produce engagement of the terminal ends of the arms with the teeth.

The arcuate outline of the bottom and leading edges 60, 62 of the lobes, and the chamfered or mitered edges 63 of the terminal ends of the arms, are consistent with the pitman-like motion recommended for the device, and contribute to the user's sense of direction in the various operations described.

Typically, the brushes 50 are in fact elongated somewhat in the direction longitudinally of the device, to enable the leading edge portions 62 of the lobes 56 to gently massage the gums as seen in FIG. 10.

Sometimes, a user may choose to brush the teeth to be cleaned when the bristle 49 are at room temperature, and then run the bristle for a few seconds under hot (or cold) tap water at a sink, to render the bristle changed in durometer for the next stage of his/her operation.

As in the earlier Applications, the hardness of the bristle may also vary from one area of each field to another. In particular, the bristle on the lobes, or the hinged bottom portions 59 of the lobes, may be still softer than the bristle employed on the main bodies of the brushes. Likewise, the density of the bristle may vary from one area to another, and once again, reference can be made to the forgoing Applications for various techniques for achieving this.

I claim:

1. In a straddle-type tooth brushing device,
means including a pair of elongated arms having brushes on the distal end portions thereof forming a head for straddling about a row of teeth to be cleaned, elongated support means including a handle, for supporting the head adjacent the row of teeth, and biasing means acting on the distal end portions of the arms from within the head to yieldably bias the brushes into engagement with the relatively inside and outside faces of the teeth when the head is straddled about the row thereof,
the arms having longitudinal axes and being rigidly interconnected with the support means so as to form relatively rigid longitudinal extensions thereof, which project from the distal end of the support means in generally spaced parallel relationship to one another, and have an elongated slot in the space therebetween which opens to the outside of the device at the distal end portions of the arms, and has a central plane therein which extends between the longitudinal axes of the arms generally parallel thereto,
the distal end portions of the arms having relatively laterally inwardly directed surfaces thereon which are relatively opposed to one another across the central plane of the slot and extend in planes generally parallel to the longitudinal axes of the arms, with relatively upper, lower and forward edges thereabout at the peripheries thereof, which are disposed relatively remote from, and adjacent to, the gum lines of the respective row of teeth being brushed, and forwardly of the surface, respectively, when the head is straddled about the row of teeth so that the central plane of the slot is aligned with the row of teeth, the brushes comprising discrete strands of thermoplastic resin material which are 47 or less in durometer on the Shore D Scale, 0.010 inch in diameter or greater at the bases thereof, and relatively upstanding on the relatively laterally inwardly directed surfaces of the distal end portions of the arms at individually spaced apart locations on the surfaces so as to be individually laterally deflectable in relation to one another, yet collectively operable on the respective surfaces to form mutually opposing fields of bristle that are firm enough for tooth brushing purposes but ultra soft to the gingival sulcus at the gum lines of the teeth when the head is straddled about a row of teeth and the brushes are engaged with the faces of the teeth, the arms being constructed of a stiff but resiliently flexible material terminating at the relatively upper, lower and forward peripheral edges of the relatively laterally inwardly directed surfaces of the distal end portions thereof, so that the respective arms are independent of one another transverse the central plane of the slot, and the distal end portions of the arms being so closely spaced apart from one another at the relatively laterally inwardly directed surfaces thereof, and so yieldably biased relatively toward one another by the biasing means, transverse the central plane of the slot in the relaxed state of the arms, that the user must forcibly wedge the teeth between the fields of bristle when inserting the teeth between the brushes to straddle the head about the row of teeth.

2. The straddle-type tooth brushing device according to claim 1 wherein the strands of bristle upstand on substrates of the same resin material which cover the relatively laterally inwardly directed surfaces of the distal end portions of the arms in their entireties.

3. The straddle-type brushing device according to claim 2 wherein the brushes comprise monoliths of the thermoplastic resin material, which substantially encircle the distal end portions of the arms at the relatively laterally inwardly and outwardly directed surfaces thereof, and the relatively upper and lower peripheral edges thereof, and have the strands of bristle relatively monolithically upstanding on the relatively opposing inside surfaces of the monoliths, for engagement with the faces of the teeth.

4. The straddle-type tooth brushing device according to claim 3 wherein the monoliths have portions thereof which project relatively outwardly beyond and below the relatively forward and lower peripheral edges of the distal end portions of the arms, and form relatively depending lobes thereon consisting of the resin material alone, for engaging the sulcus and gingiva of the teeth.

5. The straddle-type tooth brushing device according to claim 4 wherein the relatively remote outside surfaces of the monoliths have grooves thereacross which subdivide the lobes into main body portions, and bottom portions therebelow which are hinged to the main body portions of the lobes for deflection by the gums in the tooth brushing operation.

6. The straddle-type tooth brushing device according to claim 4 wherein the relatively bottom and leading edges of the lobes, relative to the gum lines of the teeth, are arcuately rounded.

7. The straddle-type tooth brushing device according to claim 1 wherein the resin material has a hardness of about 24–27 on the Shore D Scale, depending on the diameter of the strands of bristle at the bases thereof.

8. The straddle-type tooth brushing device according to claim 7 wherein the resin material has a Vicat softening temperature of about 140 degrees F. or greater.

9. The straddle-type tooth brushing device according to claim 1 wherein the resin material is a polyolefin.

10. The straddle-type tooth brushing device according to claim 1 wherein the resin material is a copolymer of ethylene and vinyl acetate, and the amount of vinyl acetate monomer in the copolymer is adjusted to constitute about 9–28% by weight of the total gross amount of the copolymer, depending upon the diameter of the strands of bristle at the bases thereof.

11. The straddle-type tooth brushing device according to claim 10 wherein the strands of bristle have a diameter of 0.040 inch at the bases thereof and the vinyl acetate monomer constitutes about 18–25% by weight of the total gross amount of the copolymer.

12. The straddle-type tooth brushing device according to claim 1 wherein the strands of bristle are tapered from the bases thereof to a lesser diameter at the tips thereof.

13. The straddle-type tooth brushing device according to claim 12 wherein the strands of bristle are conical and tapered to a point along the length thereof intermediate the bases and the tips thereof, and then tapered at an increased draft from the intermediate points thereof to the tips thereof.

14. The straddle-type tooth brushing device according to claim 1 wherein the arms are also fabricated from plastic resin material.

15. The straddle-type tooth brushing device according to claim 14 wherein the support means and the arms are fabricated as a monolithic frame having the brushes molded therearound on the distal end portions of the arms.

16. The straddle-type tooth brushing device according to claim 1 wherein the relatively laterally inwardly directed surfaces of the distal end portions of the arms are disposed at acute angles to the central plane of the slot in the direction relatively upwardly of the plane, and the strands of bristle are angled to the central plane of the slot in the opposite direction so that the fields of bristle incline apically to the gingival sulcus of the teeth, at approximately 45 degrees, when the head is straddled about a row of teeth.

17. The straddle-type tooth brushing device according to claim 16 wherein the relaxed state of the arms, the strands of bristle approach the central plane of the slot at greater than 45 degrees and interdigitate with one another at the tops of the fields.

18. The straddle-type tooth brushing device according to claim 1 wherein the arms have main portions which cantilever from the distal end of the support means and terminate independently of one another at points relatively remote from the distal end of the support means, where the slot is less than a tooth in width transverse the central plane of the slot, and the main portions of the arms have extensions thereon which cantilever relatively laterally outwardly from the terminal end portions of the main portions to greater than a tooth in width on the opposing sides of the central plane of the slot, and have relatively outboard portions thereof which project relatively outwardly beyond the terminal ends of the main portions in directions relatively away from the distal end of the support means longitudinally thereof, to form distal end portions of the arms which are spaced apart from one another at the relatively laterally inwardly directed surfaces thereof and yieldably biased toward one another at said surfaces by said main portions, transverse the central plane of the slot in the relaxed state of the arms, to the extent that the user must forcibly wedge the teeth between the fields of bristle to straddle the head about the row of teeth.

19. The straddle-type tooth brushing device according to claim 18 wherein the longitudinal axes of the arms are substantially coplanar with one another in a first cross sectional plane of the arms extending substantially normal to the central plane of the slot, and the terminal ends of the main portions of the arms are angled to the first cross sectional plane of the arms at the relatively inner peripheral edges thereof on the slot.

20. The straddle-type tooth brushing device according to claim 18 wherein the longitudinal axes of the arms are substantially coplanar with one another in a first cross sectional plane of the arms extending substantially normal to the central plane of the slot at the terminal end portions of the main portions of the arms, those sides of the terminal end portions of the main portions of the arms which are disposed relatively adjacent to the gum lines of the row of teeth being brushed, are substantially coplanar with one another in a second cross sectional plane of the arms extending substantially normal to the central plane of the slot, and the extensions of the main portions of the arms take the form of brackets which have successively interconnected inboard and outboard portions, the relatively inboard portions of which project relatively laterally outwardly from the terminal end portions of the main portions of the arms, and the relatively outboard portions of which relatively depend from the relatively inboard portions of the brackets, and cantilever relatively outwardly beyond the terminal ends of the main portions of the arms in directions relatively away from the distal end of the support means longitudinally thereof, on the opposite side of the second cross sectional plane of the arms from the first cross sectional plane thereof.

* * * * *

UNITED STATES PATENT AND TRADEMARK OFFICE
CERTIFICATE OF CORRECTION

PATENT NO. : 5,316,027
DATED : May 31, 1994
INVENTOR(S) : Ronald W. Klinkhammer

It is certified that error appears in the above-indentified patent and that said Letters Patent is hereby corrected as shown below:

Column 2, between lines 12 and 13 thereof, insert:

In the foregoing Applications, I disclosed tooth brushing devices of the foregoing type wherein the brushes were formed on the relatively opposing inside surfaces of the wings of a reentrantly folded cowling, and the wings of the cowling were interconnected with the distal end portions of the arms so that the cowling straddled the slot beween the arms. In use, the midsection at the bight between the wings, as well as pleats between the midsection and the wings, formed an articulated linkage between the arms for preserving the bias on the wings during the tooth brushing operation, and in particular as the cowling adjusted to the varying diameters of the teeth crosswise the central plane of the slot. This was a desireable function, of course, but the linkage also imposed certain limitations on the dynamics through which the device could be put in the tooth brushing operation, so that as a practical matter, there was a trade off between the function of the linkage and the limitations it imposed on the dynamics to which the device could be put.

UNITED STATES PATENT AND TRADEMARK OFFICE
CERTIFICATE OF CORRECTION

PATENT NO. : 5,316,027
DATED : May 31, 1994
INVENTOR(S) : Ronald W. Klinkhammer

It is certified that error appears in the above-indentified patent and that said Letters Patent is hereby corrected as shown below:

```
Column 13, line 47, thereof, after "straddle-type" insert --tooth--
Column 14, line 9, thereof, change "24 - 27" to read --24 - 47--
Column 14, line 57, thereof, after "wherein" insert --in--
```

Signed and Sealed this

Twenty-first Day of March, 1995

Attest:

BRUCE LEHMAN

Attesting Officer      Commissioner of Patents and Trademarks